United States Patent
McNeill et al.

(10) Patent No.: US 10,456,520 B2
(45) Date of Patent: Oct. 29, 2019

(54) STRETCHABLE ATTACHMENT APPARATUS

(71) Applicant: Clinical Biotechnology Research Institute at RSFH, Charleston, SC (US)

(72) Inventors: Lauren McNeill, Mt. Pleasant, SC (US); Christopher Lienhop, Wilmington, NC (US); Andrea H. Marshall, Mt. Pleasant, SC (US); Krista Herndon, Summerville, SC (US)

(73) Assignee: Clinical Biotechnology Research Institute at RSFH, Charleston, SC (US)

( * ) Notice: Subject to any disclaimer, the term of this patent is extended or adjusted under 35 U.S.C. 154(b) by 10 days.

(21) Appl. No.: 15/898,630

(22) Filed: Feb. 18, 2018

(65) Prior Publication Data

US 2018/0161493 A1   Jun. 14, 2018

Related U.S. Application Data

(63) Continuation-in-part of application No. 15/240,006, filed on Aug. 18, 2016, now Pat. No. 9,895,485.

(51) Int. Cl.
*A61M 5/14* (2006.01)
*A61G 7/05* (2006.01)

(52) U.S. Cl.
CPC .............. *A61M 5/1415* (2013.01); *A61G 7/05* (2013.01); *A61G 7/0503* (2013.01); *A61M 5/14* (2013.01);

(Continued)

(58) Field of Classification Search
CPC .............. A61M 5/1415; A61M 5/1417; A61M 2209/082; A61G 7/0503
See application file for complete search history.

(56) References Cited

U.S. PATENT DOCUMENTS

| | | | | |
|---|---|---|---|---|
| 1,086,442 A | * | 2/1914 | Cornelius | F16L 3/14 24/17 A |
| 1,359,329 A | * | 11/1920 | Carson | B62J 9/003 220/485 |

(Continued)

OTHER PUBLICATIONS

Whiz Tie. 5 pages. Accessed online Feb. 15, 2018 at https://www.whiztie.com/Mishler Labs, Hickory Corners, MI.

(Continued)

*Primary Examiner* — Anita M King
(74) *Attorney, Agent, or Firm* — Gregory Finch; Finch Paolino, LLC

(57) ABSTRACT

A hospital bed rail attachment apparatus constructed of molded silicone or another form of elastomeric substance. An embodiment of the present disclosure includes an elongated member having a first appendage, a second appendage, and a central portion extending between the first appendage and the second appendage. The first appendage may include a first protrusion and a first receiving portion being configured to receive the first protrusion. The second appendage may include a second protrusion and a second receiving portion being configured to receive the second protrusion. Embodiments of the present disclosure may include a pair of elongated members being configured to be selectively coupled to a container at a first end and a hospital bed rail at a second end.

16 Claims, 7 Drawing Sheets

(52) U.S. Cl.
CPC ..... *A61M 5/1417* (2013.01); *A61M 2209/082* (2013.01)

(56) References Cited

U.S. PATENT DOCUMENTS

| | | | |
|---|---|---|---|
| 2,936,980 A * | 5/1960 | Rapata | F16L 3/12 24/16 PB |
| 2,959,098 A * | 11/1960 | Hassman | G02C 3/003 24/16 PB |
| 3,231,901 A | 2/1966 | Kennedy | |
| 3,486,200 A * | 12/1969 | Orenick | B65D 63/1081 24/16 PB |
| 3,654,669 A * | 4/1972 | Fulton | B65D 63/14 24/16 PB |
| 4,001,919 A | 1/1977 | Moberg et al. | |
| 4,037,603 A * | 7/1977 | Wendorff | A61B 17/00 606/157 |
| 4,466,159 A * | 8/1984 | Burrage | B65D 63/10 24/16 PB |
| 4,823,444 A | 4/1989 | Larsen | |
| 4,832,294 A | 5/1989 | Eidem | |
| 4,910,831 A * | 3/1990 | Bingold | B65D 63/1036 128/878 |
| 4,942,644 A * | 7/1990 | Rowley | B65D 63/10 24/16 PB |
| 5,005,793 A | 4/1991 | Shillington | |
| 5,135,188 A | 8/1992 | Anderson et al. | |
| 5,159,728 A * | 11/1992 | Bingold | E05B 75/00 24/16 PB |
| D342,668 S | 12/1993 | Rose et al. | |
| 5,402,971 A | 4/1995 | Bower | |
| 5,673,829 A | 10/1997 | Hartshorn | |
| 5,699,564 A * | 12/1997 | Heh | A47D 15/00 220/495.1 |
| 5,699,642 A * | 12/1997 | McDevitt, Jr. | E04C 5/162 24/16 PB |
| D391,636 S | 3/1998 | Zwerk | |
| 5,802,888 A * | 9/1998 | Parsons | A61F 5/37 128/879 |
| 5,806,819 A | 9/1998 | Marione | |
| 6,186,454 B1 | 2/2001 | Olsen | |
| 6,364,257 B1 * | 4/2002 | Holder | F16L 3/2336 24/16 PB |
| 6,409,131 B1 | 6/2002 | Bentley et al. | |
| 6,449,808 B1 | 9/2002 | Zappa et al. | |
| 6,640,393 B2 | 11/2003 | Wendle | |
| 6,681,451 B1 | 1/2004 | Adams et al. | |
| 6,807,715 B1 * | 10/2004 | Blair | B65D 63/1027 24/16 PB |
| 6,828,509 B2 | 12/2004 | Ito et al. | |
| 7,107,654 B2 * | 9/2006 | Byers | B65D 63/109 24/16 PB |
| 7,475,859 B2 | 1/2009 | Selders | |
| D599,196 S * | 9/2009 | Ruffin | D8/356 |
| 7,731,138 B2 | 6/2010 | Wiesner et al. | |
| 7,913,959 B2 | 3/2011 | White et al. | |
| 7,959,122 B1 | 6/2011 | Clack-Hopkins | |
| 8,203,077 B2 * | 6/2012 | Honeycutt | H02G 3/32 174/135 |
| 8,245,857 B2 | 8/2012 | DiGasbarro | |
| 8,559,782 B2 * | 10/2013 | Cleofe | H02G 3/30 24/16 PB |
| D703,040 S | 4/2014 | White | |
| 9,067,717 B2 * | 6/2015 | DeMik | B65D 67/02 |
| 2002/0096608 A1 | 7/2002 | Cedarberg, III | |
| 2003/0167605 A1 | 9/2003 | Schultz | |
| 2006/0081748 A1 * | 4/2006 | Sherman | A47G 25/08 248/309.1 |
| 2008/0011907 A1 | 1/2008 | Jacobsma | |
| 2009/0277464 A1 * | 11/2009 | Chavez | A61F 5/37 128/878 |
| 2010/0243834 A1 | 9/2010 | Salser | |
| 2011/0084181 A1 | 4/2011 | Bowers et al. | |

OTHER PUBLICATIONS

EZP Portable Urinal Holder. 1 page. Accessed online Feb. 15, 2018 at http://www.urinalholder.com/ezp-urinal-holders.html. PLG Innovations, Inc. Millville, CA.

* cited by examiner

STRETCHABLE ATTACHMENT APPARATUS

CROSS-REFERENCE TO RELATED APPLICATION

The present application is a continuation-in-part of U.S. patent application Ser. No. 15/240,006, filed on Aug. 18, 2016 and entitled "Stretchable IV Pole Attachment Apparatus," which is hereby incorporated in its entirety by reference.

FIELD

The present disclosure relates to the field of medical devices accessories; in particular, attachment devices for hospital bed rails.

BACKGROUND

Infection control is an ever-increasing concern in hospital environments. Harmful infectious diseases can be spread by contact with a patient's contaminated body fluids. Healthcare providers are constantly on a quest to minimize the risk of exposure to harmful organisms. Bladder bags present a unique problem in that unlike IV bags, which hang from a hook above a patient's heart on a IV pole, bladder bags must utilize the effects of gravity and hang below the patient to function correctly. Because of this necessity, the bladder bag cannot be placed on the higher hooks of the IV pole and are generally hung over the side of the patient's bed. These bags are not sterile and function to hold the waste products from the patient. Accidental leakage from these bags can unknowingly contaminate the hospital furniture and potentially expose health workers and family member to infectious diseases.

A review of the prior art reveals several different types of fasteners for an IV pole. For example, U.S. Pat. No. 6,409,131 B1 issued to Bentley and Rosenau discloses a bracket that attaches to an elongated prop such as an electrical conduit, pipe, railing, IV stand, wheel chair frame, stake, hospital bed guards, or post is disclosed.

U.S. Pat. No. US20110084181 A1 discloses a Pole Universal Drainage Bag Holder. It works as a collaboration of the following parts: The Clamp Front Opening, the Middle Holding Section and the Clamp Handles. The clamp front opening is used to hold a catheter or I.V. bag or a drainage bag any general size.

U.S. Pat. No. US20100243834 A1 discloses an adjustable clamp that can attach to an IV pole.

U.S. Pat. No. US20080011907 A1 discloses an intravenous line organizer clamped to an IV pole.

U.S. Pat. No. 7,731,138 B2 discloses a mounting apparatus with a flexible shaft with a first end for releasable attachment to the support member and a second end for releasable attachment to the device. A generally C-shaped clamping member at the first end releasably attaches the apparatus to the support member.

U.S. Pat. No. 7,475,859 B2 discloses a band buckled around a pole. A hanger arm that has a top end attached to the band at an attachment point, and has a bottom end with a load hook.

U.S. Pat. No. 8,245,857 B2 discloses A storage device includes a locking slot formed in an upper portion adapted to receive at least a portion of the instrument to retain the instrument within the housing.

U.S. Pat. No. 4,823,444 discloses a device pertaining primarily to supplementary fastening devices in the form of a rigid or semi rigid clip having a loop shaped portion for fastening the hook of a garment hanger or other hook including device to a clothesline or other generally linear member to which the hook is hooked.

U.S. Pat. No. 20030167605 A1 discloses a fastening strap system, particularly of the hook-and-loop variety (with hooks on one side of the strap and loops on the other side), for selectively and independently binding and/or releasing a plurality of sets of essentially longitudinal objects, such as wires, from one another.

U.S. Pat. No. 6,186,454 B1 discloses a sign housing mounted to a swivally-mounted base and a pair of flexible and resilient, semi-circular parts are integrally formed with the base.

U.S. Pat. No. 5,005,793 discloses a pole clip needle cap holder.

U.S. Pat. No. 7,959,122 B1 discloses a catheter drainage bag holding assembly includes a clamp with an arcuate member having a pair of free ends. The arcuate member forms at least 60% of a complete circle. A threaded rod is threadably coupled to and extends through the arcuate member. The arcuate member is positionable on a post and the rod is abuttable against the post.

U.S. Pat. No. D391,636 S discloses a catheter pole attachment utilizing a nut and bolt anchoring system.

U.S. Pat. No. 7,913,959 B2 discloses a suction nozzle holster.

U.S. Pat. No. 5,135,188 A discloses a bundling strap for enclosing an article such as a wire or group of wires comprising a strap of flexible material having integrally formed along one face thereof a row of ratchet-like teeth, an enclosure formed at one end of said strap and projecting in a direction transverse thereto.

U.S. Pat. No. 3,231,901 A discloses a drain bag hanger which utilizes metal clamps and link chain.

U.S. Pat. No. US 20020096608 A1 discloses a holder with a base rotatably mounted to the IV stand. An arm is supported by the base and extends away from the base such that the arm holds the cords and the tubes extending from the medical apparatus.

The patent documents above disclose a myriad of attachment mechanisms to be used on an IV pole. However, due to the nature of their design having multiple parts and crevices, a large surface area is created that is not easily decontaminated for infection control purposes. In addition, many of the devices are made of materials in which regular disposal would not be economically efficient.

In addition to attachment mechanisms for IV poles, medical personnel commonly attach a multitude of various objects to different surfaces in a hospital room environment. One such surface is a bed rail of a hospital bed. As with prior art solutions for attachment mechanisms to be used on an IV pole, prior art solutions for attachment mechanisms to be used hospital bed rails encounter similar problems with respect to effective decontamination and economically efficient regular disposal.

Through applied effort, ingenuity, and innovation, Applicant has identified a number of deficiencies and problems with infection control with regards to the attachment mechanisms for hospital bed rails. Applicant has developed a solution to address these deficiencies and problems, and is embodied by the present invention, which is described in detail below.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

An object of the present disclosure is the continuous molded structure of the body that allows for easy decontamination of a hospital bed rail attachment apparatus.

Another object of the present disclosure is that the elastomeric material and simple body design make disposal of the hospital bed rail attachment apparatus economically feasible.

Another object of the present disclosure is a hospital bed rail attachment apparatus being constructed of an elastomeric material that enables the hospital bed rail attachment apparatus to maintain a sturdy connection with the hospital bed rail.

An embodiment of the present disclosure is molded into a single continuous elastomeric body. This allows for easy decontamination due to a smooth, continuous construction. In addition, the elastomeric design and construction allows for economic efficiency to regularly discard and replace the apparatus.

A specific embodiment of the present disclosure includes a hospital bed rail attachment apparatus comprising a unitary body constructed of an elastomeric material, the unitary body comprising an elongated member having a first appendage portion, a second appendage portion, and a central portion extending between the first appendage portion and the second appendage portion; a first protrusion disposed on the first appendage portion, the first protrusion being substantially rectangular in shape; a first receiving portion being proximally disposed on the first appendage portion in relation to the first protrusion to define a first attachment area extending between the first receiving portion and the first protrusion, the first receiving portion defining an aperture being configured to receive the first protrusion; a second protrusion disposed on the second appendage portion, the second protrusion being substantially rectangular in shape; and, a second receiving portion being proximally disposed on the second appendage portion in relation to the second protrusion to define a second attachment area extending between the second receiving portion and the second protrusion, the second receiving portion defining an aperture being configured to receive the second protrusion.

Another specific embodiment of the present disclosure includes a hospital bed rail attachment apparatus comprising a pair of elongated members constructed of a molded elastomeric material, each elongated member in the pair of elongated members having a first appendage portion, a second appendage portion, and a central portion extending between the first appendage portion and the second appendage portion; a first protrusion disposed on the first appendage portion, the first protrusion being substantially rectangular in shape; a first receiving portion being proximally disposed on the first appendage portion in relation to the first protrusion to define a first attachment area extending between the first receiving portion and the first protrusion, the first receiving portion defining an aperture being configured to receive the first protrusion; a second protrusion disposed on the second appendage portion, the second protrusion being substantially rectangular in shape; and, a second receiving portion being proximally disposed on the second appendage portion in relation to the second protrusion to define a second attachment area extending between the second receiving portion and the second protrusion, the second receiving portion defining an aperture being configured to receive the second protrusion; and, a container selectively coupled to each elongated member in the pair of elongated members at the first attachment area or the second attachment area.

The foregoing has outlined rather broadly the more pertinent and important features of the present invention so that the detailed description of the invention that follow ay be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The above and other objects, features and advantages of the present disclosure will be more apparent from the following detailed description taken in conjunction with the accompanying drawings, in which.

DETAILED DESCRIPTION

Figure 1:
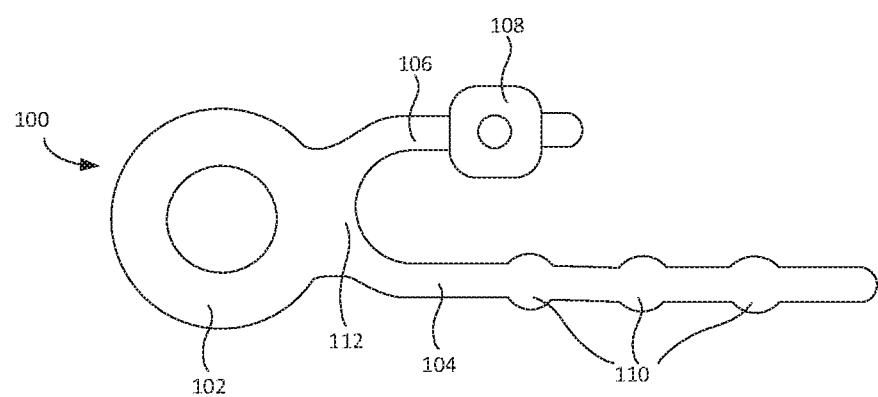
FIG. 1 is a perspective view of the IV pole attachment apparatus according to an embodiment of the present disclosure.

Exemplary embodiments are described herein to provide a detailed description of the present disclosure. Variations of these embodiments will be apparent to those of skill in the art. Moreover, certain terminology is used in the following description for convenience only and is not limiting. For example, the words "right," "left," "top," "bottom," "upper," "lower," "inner" and "outer" designate directions in the drawings to which reference is made. The word "a" is defined to mean "at least one." The terminology includes the words above specifically mentioned, derivatives thereof, and words of similar import.

Embodiments of the present disclosure provide for a disposable IV pole attachment apparatus. Embodiments of the present disclosure solve problems associated with the prior art IV pole attachment devices. Most of the designs of the prior art attachment devices are not conformed to hold bladder bags for patients to IV poles. The designs that could be utilized either have large surface areas with various moving parts which make them difficult to decontaminate effectively, or the materials used to make them are not conducive to the device being manufactured as a disposable product. A disposable attachment apparatus is desirable as the contents of a bladder bag can accidentally leak onto the structure to which it is attached. Harmful bacteria and viruses can be secreted in body fluids; therefore, it is important to decontaminate any items exposed to body fluids for proper infection control. Prior art attachment devices present with various hooks and screws that increase the surface area of the device and allow for small crevices, which can be difficult to decontaminate. Without proper infection control, healthcare workers and subsequent patients and visitors are placed at risk.

Another problem with the prior art is the complex design and materials used to make the attachment devices. An IV Pole attachment with various hooks and buckles is not as easily manufactured as one molded into a single piece. In addition, attachment devices made of metal are costlier to manufacture and are generally recycled and not disposed.

Embodiments of the present disclosure seek to overcome the deficiencies of the prior art and provide a more efficient, cost effective, and safe IV pole attachment apparatus. According to various embodiments of the present disclosure, the problem of large surface area and crevices is solved by the molded continuous body of the IV Pole attachment apparatus.

The continuous body of the apparatus can be easily disinfected or wiped down, as there are no parts containing crevices that could hold contaminated fluids.

According to various embodiments of the present disclosure, the problem of complex design is solved by a simple one-piece body of molded elastomeric material. Further, this elastomeric material is inexpensive which in turn makes it economically feasible to produce the apparatus as a disposable product. A disposable product is always the preferred method of infection control in hospital settings.

Referring now to FIG. 1, a top perspective view of an IV pole attachment apparatus 100 is shown. According to an embodiment, device 100 is generally comprised of an attachment portion 102, a first appendage 104, a second appendage 106, a receiving portion 108, protrusions 110, and an appendage connection portion 112. The IV pole attachment apparatus 100 is constructed of silicone or another form of elastomeric substance. The elastomeric substance of IV pole attachment apparatus 100 may be alternatively constructed from a flexible antimicrobial substance or combination thereof. One end of IV pole attachment apparatus 100 is the attachment portion 102. Attachment portion 102 is ring-shaped; it may be alternatively constructed in a different geometric shape, such as square, triangle, rectangle, irregular, and the like. The shape of attachment portion 102 can be any commercially viable shape capable of receiving a hook from a bladder bag. The silicone of attachment portion 102 is substantially thicker than the silicone of the appendage portions. The silicone of attachment portion 102 may be approximately 20% to 200% thicker than the silicone of the appendage portions 104 and 106. This increase in thickness allows the attachment portion 102 to support the weight of an attached bladder bag. Attachment portion 102 is seamlessly molded to the appendage connection portion 112. Appendage connection portion 112 is seamlessly connected to the first appendage 104 and the second appendage 106. The first appendage 104 contains three spaced protrusions 110 molded into the appendage in a linear consecutive arrangement. The first appendage 104 may be alternatively constructed to contain more or less protrusions, depending on the length of first appendage 104.

The protrusions 110 are spherical in shape. The protrusions 110 may be alternatively constructed in various shapes, such as cylindrical, irregular, star-shaped, and the like. The first appendage 104 is pulled through the aperture of the receiving portion 108. The protrusions 110 that line the first appendage 104 are greater in diameter than the aperture of the receiving portion 108. The elastomeric material allows the protrusions 110 to be forced through the aperture of the receiving portion 108. The greater diameter of the protrusions 110 keeps them from easily passing back thorough the aperture of the receiving portion 108 and allows for a buckling action that secures the IV pole attachment apparatus 100 to an IV pole. The second appendage 106 is approximately half the length of the first appendage 104. The second appendage 106 may be alternatively constructed in a longer length. The second appendage 106 contains a receiving portion 108 seamlessly molded into the appendage. The receiving portion 108 is square. The receiving portion 108 may be alternatively constructed in another geometric shape. The receiving portion 108 is constructed to provide for an aperture capable of receiving a spherical protrusion 110 from first appendage 104. The receiving portion 108 may be alternatively constructed to provide for an aperture capable of receiving a protrusion of a different geometric shape. The diameter of the aperture within the receiving portion 108 is less than the diameter of the protrusions 110.

Figure 2:
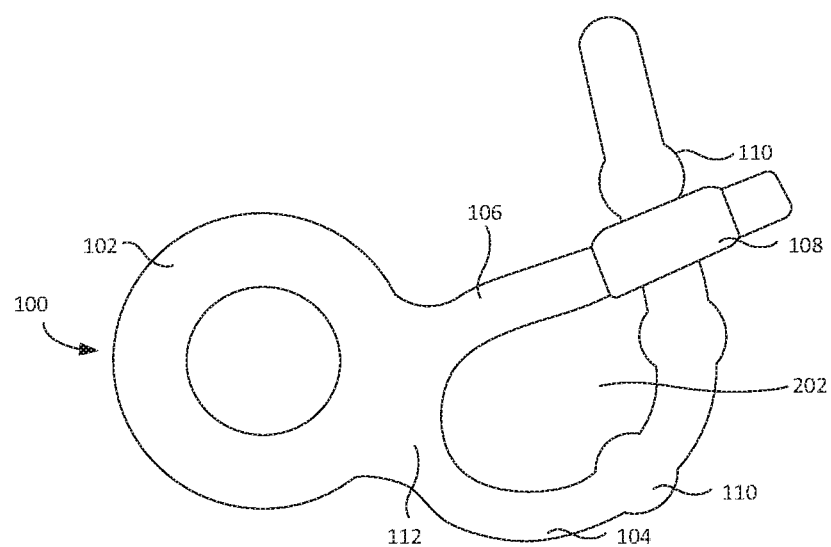
FIG. 2 is a perspective view thereof, according to an embodiment.

Referring now to FIG. 2, a top perspective view of the IV pole attachment apparatus 100 in a locking position is demonstrated. According to an embodiment of the present disclosure, protrusions 110 are molded into the first appendage 104. A protrusion 110 on the first appendage 104 is pulled through the aperture of the receiving portion 108. The greater diameter of the protrusion 110 allows the first appendage 104 and the second appendage 106 to maintain a buckled position as shown. This buckled position causes the appendage connection portion 112 to form a U-shape attachment loop 202. The attachment loop 202 fits flush against the IV pole.

Figure 3:
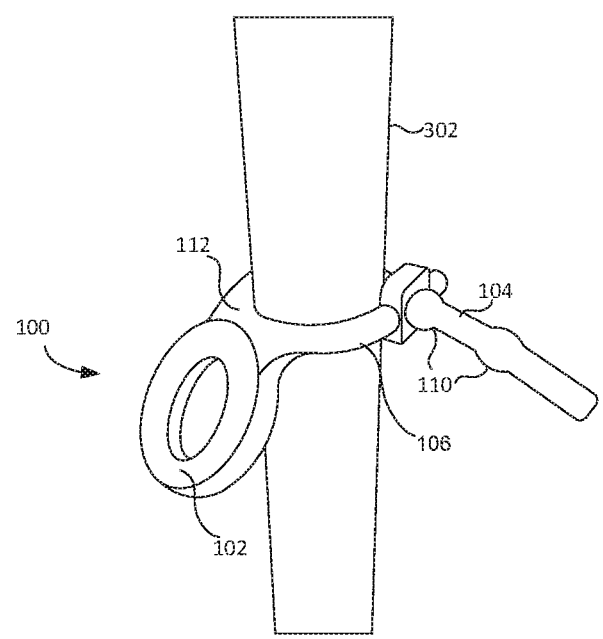
FIG. 3 is a perspective in-use view thereof, according to an embodiment.

FIG. 3 is a side perspective view of the IV pole attachment apparatus 100 attached to an IV pole 302. The IV pole attachment apparatus 100 is buckled onto the IV pole 302 by placing the appendage connection portion 112 flush against the IV pole 302 and pulling the first appendage 104 through the aperture of the receiving portion 108 of the second appendage 106. The sides of the receiving portion 108 must be pulled apart in order to increase the diameter of the aperture and allow a protrusion 110 on the first appendage 104 to pass through. Once the protrusion 110 is pulled through the aperture of the receiving portion 108, the elastomeric material reforms a smaller diameter aperture, in turn restricting the passage of the protrusion 110 back through the receiving portion. As shown, the IV pole attachment apparatus 100 is in this buckled position. The apparatus connection portion 112, the second appendage 106, and the upper portion of the first appendage 104 sit flush against the IV pole 302 when the IV pole attachment apparatus 100 is in the buckled position. As shown, attachment portion 102 is formed as a circular structure thicker in elastomeric material than the first appendage 104 and the second appendage 106. This thickness allows the attachment portion 102 to withstand the weight of a filled bladder bag. The IV pole attachment apparatus 100 is easily removed from the IV pole 302 for decontamination or disposal. To remove the IV pole attachment apparatus 100, the elastomeric material of the receiving portion 108 is pulled apart to form an aperture large enough for the first appendage 104 and the protrusion 110 to pass back through. The unbuckling releases the IV pole attachment apparatus 100 from the IV pole 302.

Figure 4:
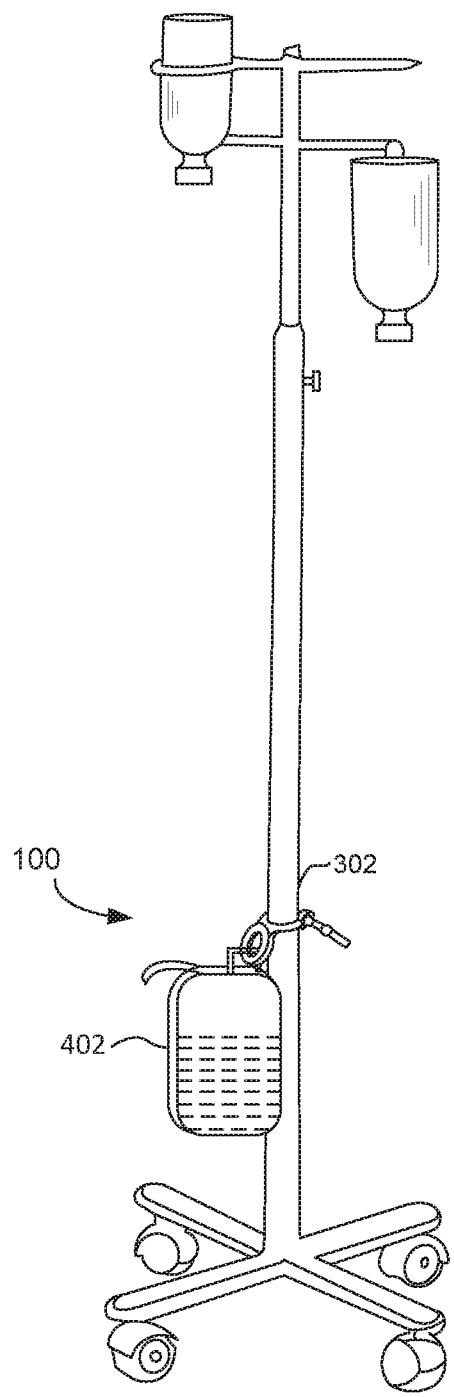
FIG. 4 is a perspective in-use view thereof, according to an embodiment.

FIG. 4 is a perspective in-use view of the IV pole attachment apparatus 100. FIG. 4 demonstrates how the bladder bag 402 hooks onto the IV pole attachment apparatus 100. This provides for a more sanitary way to maintain the bladder bag 402 while still having the bladder bag 402 positioned below the patient for proper functioning. The IV pole attachment apparatus 100 provides a place to hang the bladder bag other than on the patient or the room furniture. The use of the IV pole attachment apparatus 100 improves infection control by preventing contamination of the patient's clothing and furniture due to accidental leakage. Due to the simple continuous body of the IV pole attachment apparatus 100, it is easily disinfected or disposed of after use.

Hospital Bed Rail Attachment Apparatus

An alternative embodiment of the present disclosure provides for a disposable hospital bed rail attachment apparatus. Embodiments of the present disclosure solve problems associated with the prior art hospital bed rail attachment devices. Most of the designs of the prior art attachment devices either have large surface areas with various moving parts which make them difficult to decontaminate effectively, or the materials used for construction are not conducive to being manufactured as a disposable product. A disposable attachment apparatus is desirable as the surfaces adjacent to a hospital bed are prone to contamination. According to various embodiments of the present disclosure, the problem of multi-piece construction is solved by a one-piece body of molded elastomeric material. Elastomeric material is inexpensive which makes regular disposal and replacement of the apparatus economically feasible, as compared to prior art solutions.

Figure 5:
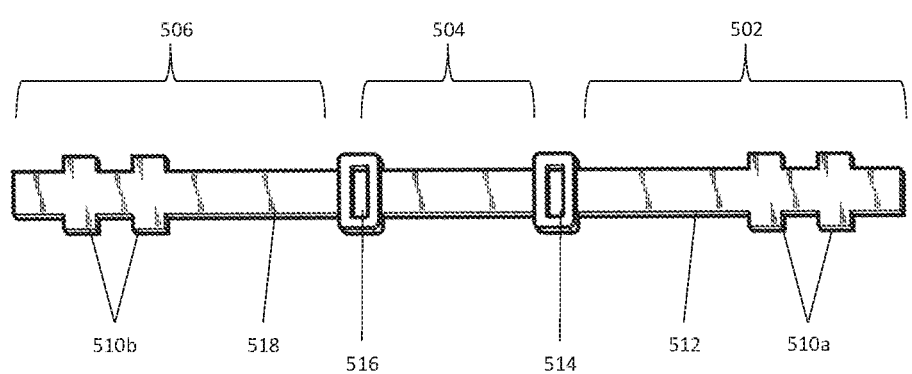
FIG. 5 is a perspective view of a hospital bed rail attachment apparatus, according to an alternative embodiment of the present disclosure.

Referring now to FIG. 5, a perspective view of a hospital bed rail attachment apparatus 500 is show. According to an embodiment, hospital bed rail attachment apparatus 500 is configured as an elongated member constructed of a molded elastomeric material. Hospital bed rail attachment apparatus 500 may be generally comprised of a first appendage portion 502, a second appendage portion 506, and a central portion 504 extending between first appendage portion 502 and second appendage portion 506. First appendage portion 502 may be configured to define at least one protrusion 510a and a first receiving portion 514. A first attachment area 512 may be defined by a length of first appendage portion 502 extending between protrusion 510a and first receiving portion 514. Second appendage portion 506 may be configured to define at least one protrusion 510b and a second receiving portion 516. A second attachment area 518 may be defined by a length of second appendage portion 506 extending between protrusion 510b and second receiving portion 516.

Protrusions 510 may be substantially rectangular in shape; however, the shape of protrusions 510 is a design choice, and may be configured as a multitude of alternative shapes. In an embodiment, hospital bed rail attachment apparatus 500 includes two protrusions 510a disposed on first appendage portion 502, and two protrusions 510b disposed on second appendage portion 506. Alternatively, there may be as few as one protrusion 510 or a plurality of protrusions 510 disposed on either of first appendage portion 502 or second appendage portion 506. Protrusions 510 should be wider in width than that of central portion 504. First receiving portion 514 and second receiving portion 516 each have an aperture configured to receive protrusions 510. The aperture of first receiving portion 514 and second receiving portion 516 may be substantially oblong in shape; however, the shape of the aperture of first receiving portion 514 and second receiving portion 516 is a design choice, and may be configured as any shape suitable to receive and hold protrusions 510. Hospital bed rail attachment apparatus 500 is configured such that a user may insert the end of first appendage portion 502 into the aperture of first receiving portion 514, and pull protrusion 510 therethrough. Likewise, hospital bed rail attachment apparatus 500 is configured such that a user may insert the end of second appendage portion 506 into the aperture of second receiving portion 516, and pull protrusion 510 therethrough. The elastomeric material utilized in the construction of hospital bed rail attachment apparatus 500 should be of a hardness and elasticity such that protrusions 510 are substantially stretchable to be pulled through first receiving portion 514 or second receiving portion 516, but are substantially hard enough to maintain a connection with first receiving portion 514 or second receiving portion 516 when engaged to support a desired load capacity of an attached object.

Figure 6:
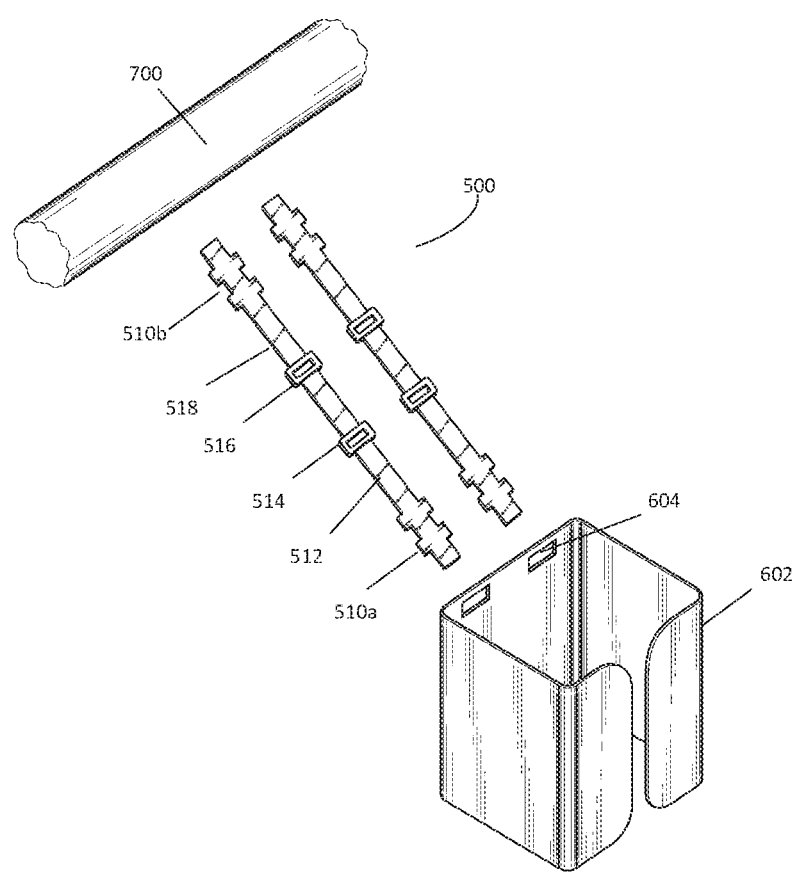
FIG. 6 is a perspective view of a hospital bed rail attachment apparatus used in combination with an attachable container; and, FIG. 7 is a perspective in-use view thereof, according to the embodiment of FIG. 6.
Figure 7:
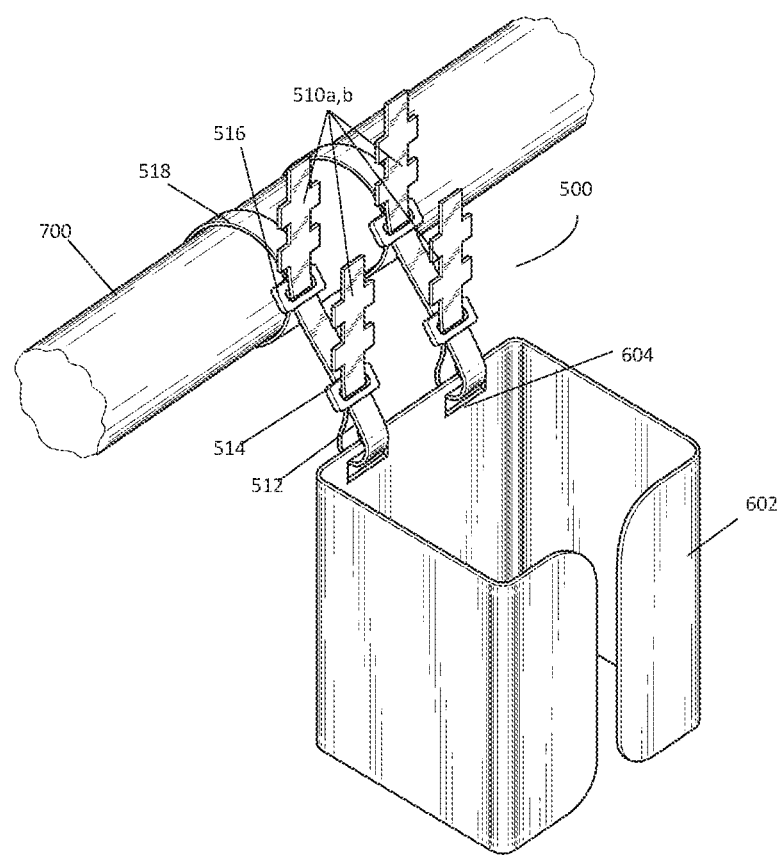

Referring now to FIGS. 6 and 7, a perspective view of hospital bed rail attachment apparatus 500 as used in combination with an attachable container 602 is shown. Referring first to FIG. 6, a pair of hospital bed rail attachment apparatuses 500 utilized to attach a container 602 to a hospital bed rail 700. According to an embodiment, a user inserts the end of first appendage portion 502 into an opening 604 of the container 602, and pulls protrusion 510 therethrough. The user then inserts the end of first appendage portion 502 into the aperture of first receiving portion 514 and pulls protrusion 510a therethrough to define a loop with first attachment area 512. The user repeats this process with hospital bed rail attachment apparatuses 500. The pair of hospital bed rail attachment apparatuses 500 are thereby securely connected to container 602 (as shown in FIG. 7). To securely attach hospital bed rail attachment apparatuses 500, the user wraps a second appendage portion 506 around a circumference of hospital bed rail 700. The user then inserts the end of second appendage portion 506 into the aperture of second receiving portion 516 and pulls protrusion 510b therethrough to define a loop with second attachment area 518. The user repeats this process with hospital bed rail attachment apparatuses 500. The pair of hospital bed rail attachment apparatuses 500 are thereby securely connected to hospital bed rail 700 (as shown in FIG. 7). To disconnect hospital bed rail attachment apparatuses 500 from container 602, the user pulls protrusion 510a back through the aperture of first receiving portion 514 to disconnect the loop defined by first attachment area 512. To disconnect hospital bed rail attachment apparatuses 500 from hospital bed rail 700, the user pulls protrusion 510b back through the aperture of second receiving portion 516 to disconnect the loop defined by second attachment area 518. Hospital bed rail attachment apparatuses 500 can be wiped clean or discarded and replaced when contaminated.

The present disclosure includes that contained in the appended claims as well as that of the foregoing description. Although this invention has been described in its exemplary forms with a certain degree of particularity, it is understood that the present disclosure of has been made only by way of example and numerous changes in the details of construction and combination and arrangement of parts may be employed without departing from the spirit and scope of the invention.

What is claimed is:

1. A hospital bed rail attachment apparatus comprising:
 a unitary body molded of an elastomeric material and having a smooth and continuous construction, the unitary body comprising an elongated member having a first appendage portion, a second appendage portion, and a central portion extending between the first appendage portion and the second appendage portion;

a first protrusion disposed on the first appendage portion, the first protrusion being substantially rectangular in shape and wider than a width of the central portion;

a first receiving portion being proximally disposed on the first appendage portion in relation to the first protrusion to define a first attachment area extending between the first receiving portion and the first protrusion, the first receiving portion defining an aperture configured to receive the first protrusion;

a second protrusion disposed on the second appendage portion, the second protrusion being substantially rectangular in shape and wider than the width of the central portion; and, a second receiving portion being proximally disposed on the second appendage portion in relation to the second protrusion to define a second attachment area extending between the second receiving portion and the second protrusion, the second receiving portion defining an aperture configured to receive the second protrusion.

2. The hospital bed rail attachment apparatus of claim 1 wherein the first protrusion is selectively configured to extend through the aperture of the first receiving portion such that the first attachment area is configured to define a loop.

3. The hospital bed rail attachment apparatus of claim 1 wherein the second protrusion is selectively configured to extend through the aperture of the second receiving portion such that the second attachment area is configured to define a loop.

4. The hospital bed rail attachment apparatus of claim 1 wherein the aperture of the first receiving portion and the aperture of the second receiving portion is substantially oblong in shape.

5. The hospital bed rail attachment apparatus of claim 1 wherein at least the first appendage portion or the second appendage portion is configured to be selectively coupled around a circumference of a hospital bed rail.

6. The hospital bed rail attachment apparatus of claim 1 further comprising at least two protrusions disposed on the first appendage portion.

7. The hospital bed rail attachment apparatus of claim 1 further comprising at least two protrusions disposed on the second appendage portion.

8. The hospital bed rail attachment apparatus of claim 1 wherein at least one of the first protrusion or the second protrusion is selectively configured to extend through the aperture of the first receiving portion or the second receiving portion, respectively, such that the first attachment area or the second attachment area is configured to define a loop, said loop being configured to be selectively coupled around a circumference of the hospital bed rail.

9. A hospital bed rail attachment apparatus comprising:

a pair of elongated members molded of an elastomeric material and having a smooth and continuous construction, each elongated member in the pair of elongated members having a first appendage portion, a second appendage portion, and a central portion extending between the first appendage portion and the second appendage portion, each elongated member in the pair of elongated members being constructed of a unitary body;

a first protrusion disposed on the first appendage portion, the first protrusion being substantially rectangular in shape and wider than a width of the central portion;

a first receiving portion being proximally disposed on the first appendage portion in relation to the first protrusion to define a first attachment area extending between the first receiving portion and the first protrusion, the first receiving portion defining an aperture being configured to receive the first protrusion;

a second protrusion disposed on the second appendage portion, the second protrusion being substantially rectangular in shape and wider than the width of the central portion;

a second receiving portion being proximally disposed on the second appendage portion in relation to the second protrusion to define a second attachment area extending between the second receiving portion and the second protrusion, the second receiving portion defining an aperture being configured to receive the second protrusion; and, a container selectively coupled to each elongated member in the pair of elongated members at the first attachment area or the second attachment area, each elongated member in the pair of elongated members being configured to be selectively coupled to a hospital bed rail at the first attachment area or the second attachment area.

10. The hospital bed rail attachment apparatus of claim 9 wherein at least the first appendage portion or the second appendage portion of each elongated member in the pair of elongated members is configured to be selectively coupled around a circumference of the hospital bed rail.

11. The hospital bed rail attachment apparatus of claim 9 wherein the first protrusion of each elongated member in the pair of elongated members is selectively configured to extend through the aperture of the first receiving portion of each elongated member such that the first attachment area of each elongated member is configured to define a loop.

12. The hospital bed rail attachment apparatus of claim 9 wherein the second protrusion of each elongated member in the pair of elongated members is selectively configured to extend through the aperture of the second receiving portion of each elongated member such that the second attachment area of each elongated member is configured to define a loop.

13. The hospital bed rail attachment apparatus of claim 9 wherein the aperture of the first receiving portion and the aperture of the second receiving portion of each elongated member in the pair of elongated members is substantially oblong in shape.

14. The hospital bed rail attachment apparatus of claim 9 further comprising at least two protrusions disposed on the first appendage portion of each elongated member in the pair of elongated members.

15. The hospital bed rail attachment apparatus of claim 9 further comprising at least two protrusions disposed on the second appendage portion of each elongated member in the pair of elongated members.

16. The hospital bed rail attachment apparatus of claim 9 wherein at least one of the first protrusion or the second protrusion of each member in the pair of elongated members is selectively configured to extend through the aperture of the first receiving portion or the second receiving portion of each elongated member, respectively, such that the first or second attachment area of each elongated member is configured to define a loop, said loop being configured to be selectively coupled around a circumference of the hospital bed rail.

\* \* \* \* \*